(12) United States Patent
Zambelli

(10) Patent No.: US 11,428,397 B2
(45) Date of Patent: Aug. 30, 2022

(54) LIGHTING DEVICE WITH AIR FILTERING SYSTEM

(71) Applicant: CAIMI BREVETTI S.P.A., Nova Milanese (IT)

(72) Inventor: Alessandro Zambelli, Canneto Sull'oglio (IT)

(73) Assignee: CAIMI BREVETTI S.p.A., Nova Milanese (IT)

(*) Notice: Subject to any disclaimer, the term of this patent is extended or adjusted under 35 U.S.C. 154(b) by 0 days.

(21) Appl. No.: 17/601,807

(22) PCT Filed: Apr. 6, 2020

(86) PCT No.: PCT/EP2020/059814
§ 371 (c)(1),
(2) Date: Oct. 6, 2021

(87) PCT Pub. No.: WO2020/207985
PCT Pub. Date: Oct. 15, 2020

(65) Prior Publication Data
US 2022/0178531 A1    Jun. 9, 2022

(30) Foreign Application Priority Data

Apr. 8, 2019  (IT) .................. 102019000005344

(51) Int. Cl.
*F21V 29/60*    (2015.01)
(52) U.S. Cl.
CPC ........... *F21V 29/60* (2015.01); *A61L 2209/14* (2013.01)
(58) Field of Classification Search
CPC .............................. F21V 29/60; A61L 2209/14

USPC ......................................................... 362/253
See application file for complete search history.

(56) References Cited

U.S. PATENT DOCUMENTS

| 2,790,510 | A | 4/1957 | Brabec |
| 7,083,659 | B1 | 8/2006 | Joyce et al. |
| 2012/0275960 | A1* | 11/2012 | Seck ............. A62B 15/00 422/121 |

FOREIGN PATENT DOCUMENTS

| CN | 207349842 | 5/2018 |
| EP | 1 207 220 A1 | 5/2002 |
| EP | 1 207 220 B1 | 1/2008 |

(Continued)

OTHER PUBLICATIONS

International Search Report for PCT/EP2020/059814, dated Jun. 8, 2020, 5 pages.

(Continued)

*Primary Examiner* — Sean P Gramling
(74) *Attorney, Agent, or Firm* — Nixon & Vanderhye P.C.

(57) ABSTRACT

The present invention relates to a lighting device comprising a main body (10), a lighting body (20) and an anodized metal filter (30), in which said metal comprises a superficial porous layer of an oxide of said metal comprising at least one antimicrobial substance. In one embodiment, the filter comprises a plurality of threadlike elements of said anodized metal, at least partially in non-permanent contact with each other, randomly deformed to form a plurality of non-linear pathways. The air to be treated passes through said filter owing to the effect of a difference in temperature and/or the action of a mechanical device. In other embodiments, the filter comprises a metal sheet with holes.

12 Claims, 7 Drawing Sheets

(56) References Cited

FOREIGN PATENT DOCUMENTS

JP      H10-38361     2/1998
WO    2013/155618   10/2013

OTHER PUBLICATIONS

Written Opinion of the ISA for PCT/EP2020/059814, dated Jun. 8, 2020, 5 pages.

* cited by examiner

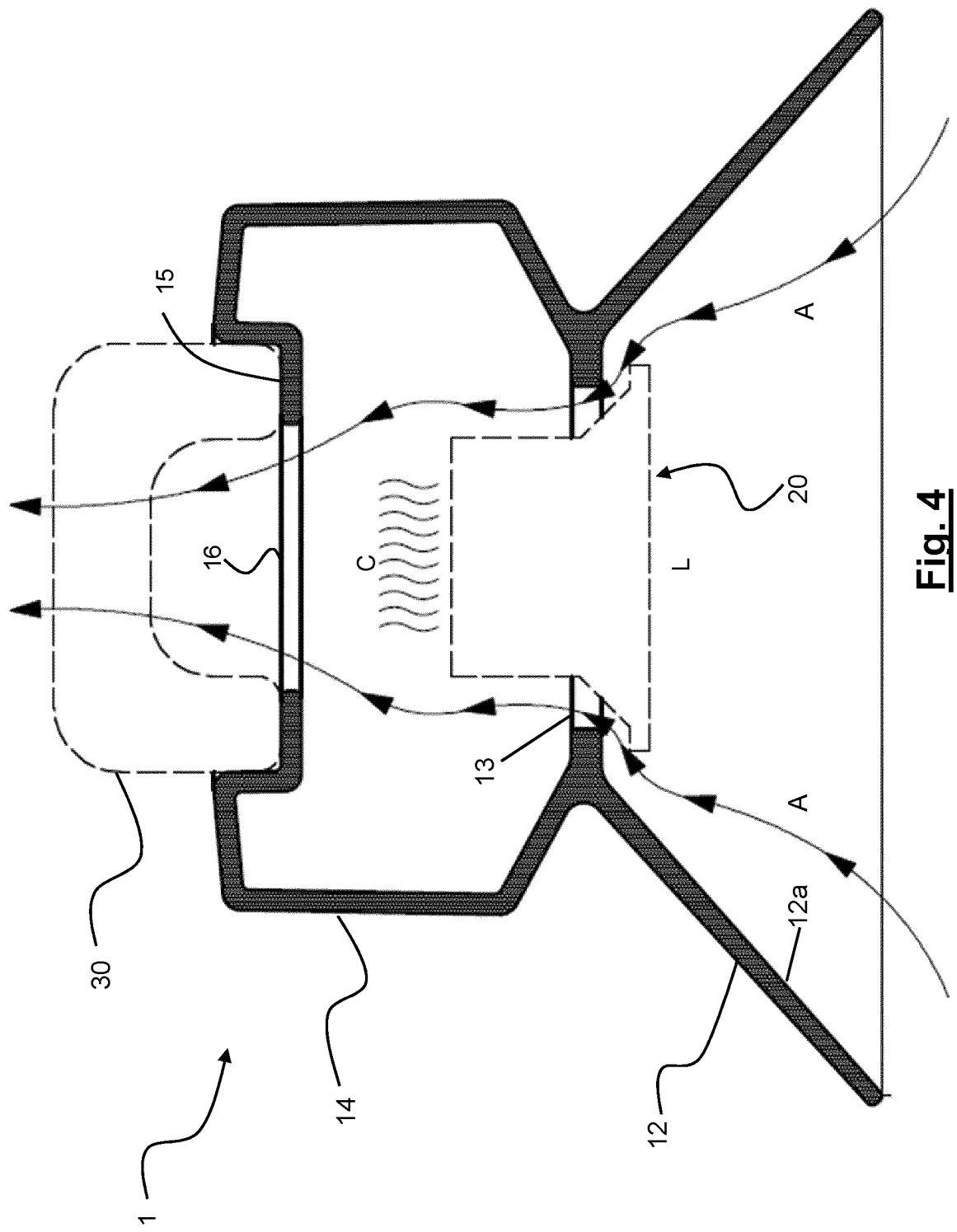

LIGHTING DEVICE WITH AIR FILTERING SYSTEM

This application is the U.S. national phase of International Application No. PCT/EP2020/059814 filed 6 Apr. 2020, which designated the U.S. and claims priority to IT Patent Application No. 102019000005344 filed 8 Apr. 2019, the entire contents of each of which are hereby incorporated by reference.

FIELD OF THE INVENTION

The present invention relates to the sector of lighting devices, such as lamps and chandeliers. In particular, it relates to a lighting device with an air filtering system, for example a filter having antimicrobial properties.

PRIOR ART

A lighting device is typically configured to illuminate an object, a surface or a room. For example, a suspended chandelier is configured to illuminate the room in which it is installed.

A lighting device may comprise a lighting body based on various types of technology. The lighting body may be, for example, a conventional incandescent, LED, fluorescent or other type of light bulb.

Although the present-day technologies have reduced significantly the heat generated by a lighting body, the lighting body of a lighting device in any case generates heat. The air in the vicinity of the lighting body heats up and generates air flows. Typically the heated air tends to rise.

SUMMARY OF THE INVENTION

The Applicant has observed the movement of air in the vicinity of a lighting body and has assessed the possibility of exploiting this movement of air in order to improve the quality of the air in a room.

In particular, the Applicant has considered the possibility of providing an air filtering system in a lighting device.

It is known that there exists in the art a vast range of filters and filtering systems for fluids, such as water or air, for domestic applications, in public places or industrial premises, such as air conditioning, extraction and/or recirculation systems, as well as systems for circulating sanitary and/or drinking water.

In all these applications there exists the need to separate the fluids from particulate matter of various sizes and kinds, as well as oily residue, for example resulting from fumes produced during the cooking of food, or other undesirable substances.

Also known for such applications are filters consisting at least partly of metal, for example steel and/or aluminum, grilles.

Aluminum, in particular, is one of the most widely used metals in the world, being relatively low-cost, easy to machine and versatile. It is a metal which is light, but has an excellent corrosion-resistance and durability, high thermal and electrical conductivity and excellent malleability and ductility.

Aluminum is moreover a non-pyrophoric metal, does not pose particular problems as regards toxicity and may be easily combined with other metals to produce alloys. Finally, different treatments known in the art are able to modify its properties, in particular its resistance and hardness, and its aesthetic appearance, using simple and low-cost processes.

Anodization, which is an irreversible electrolytic passivation treatment, is a process commonly used to increase the corrosion and wear resistance of various metals, including aluminum and its alloys. This process involves the formation of a thin, non-removable layer of oxide on the surface of the treated metal. This layer, which penetrates at least partly into the thickness of the metal, is by nature porous and therefore the anodized article must be subsequently subjected to further treatment useful for sealing the pores which have formed and, optionally, obtaining a particular color.

In the light of the above, the Applicant has considered the problem of providing a lighting device with a filtering system able to exert, in addition to a mechanical filtering action, also an effective antimicrobial action.

During the last few years post-anodization treatments have been developed, these being able to use the pores present in the superficial layer of metal oxide in order to provide the metal with antimicrobial properties. After anodization, the metal is treated with substances having antimicrobial properties which fill the pores formed in the superficial oxide layer. A subsequent sealing treatment ensures that these substances remain on the surface of the treated metal, which therefore maintains all the chemical-physical properties which are typical of anodized metal, while acquiring antimicrobial properties.

Treatments of this type on aluminum or aluminum alloy substrates are for example described in EP1207220B1.

The Applicant has now found that by using a metal which has been subjected to antimicrobial anodization treatment it is possible to obtain filters able to exert an efficient antimicrobial action.

According to the present invention, therefore, the aforementioned problem is solved by a lighting device comprising a metal filter, for example made of aluminum or aluminum alloy, anodized by means of antimicrobial anodization treatment, said filter comprising a plurality of randomly deformed threadlike elements, said threadlike elements being at least partially in contact with each other so as to form a plurality of non-linear pathways, in which said contact between two or more threads is of a non-permanent nature.

Therefore, according to a first aspect, the present invention relates to a lighting device comprising a main body, a lighting body and an anodized metal filter for treating air, wherein said metal comprises a superficial porous layer of an oxide of said metal comprising at least one antimicrobial substance.

According to embodiments, the filter comprises a metal sheet with holes.

In embodiments, the filter comprises a plurality of threadlike elements of said anodized metal, at least partially in non-permanent contact with each other, randomly deformed to form a plurality of non-linear pathways and/or a plurality of sheet metal disks with holes.

The metal may be aluminum or aluminum alloy.

The antimicrobial substance may consist of silver ions.

The threadlike elements may be present in the form of woven elements. The woven elements may be sections of metallic mesh.

The woven elements may have a flat or tubular form.

According to embodiments, the threadlike elements are deformed by means of pressing.

The superficial porous layer may be obtained on the finished filter, before or after pressing.

The superficial porous layer may be at least partially sealed.

Advantageously a channel for channeling air to be treated towards said filter may be provided.

The air to be treated may pass through said filter owing to the effect of a difference in temperature and/or the action of a mechanical device, for example a fan.

According to embodiments, the disks are arranged so that at least one hole in a first disk is not axially aligned with a corresponding hole in a second adjacent disk and/or a hole in a first disk has a different diameter from the diameter of a corresponding hole in a second adjacent disk. In this way winding paths for the air are created.

BRIEF DESCRIPTION OF THE FIGURES

The present invention will become completely clear from the following detailed description, provided purely by way of a non-limiting example, to be read with reference to the attached drawings, in which:

FIG. 4 shows a schematic section through the lighting device according to FIG. 1;

DETAILED DESCRIPTION

Figure 1:
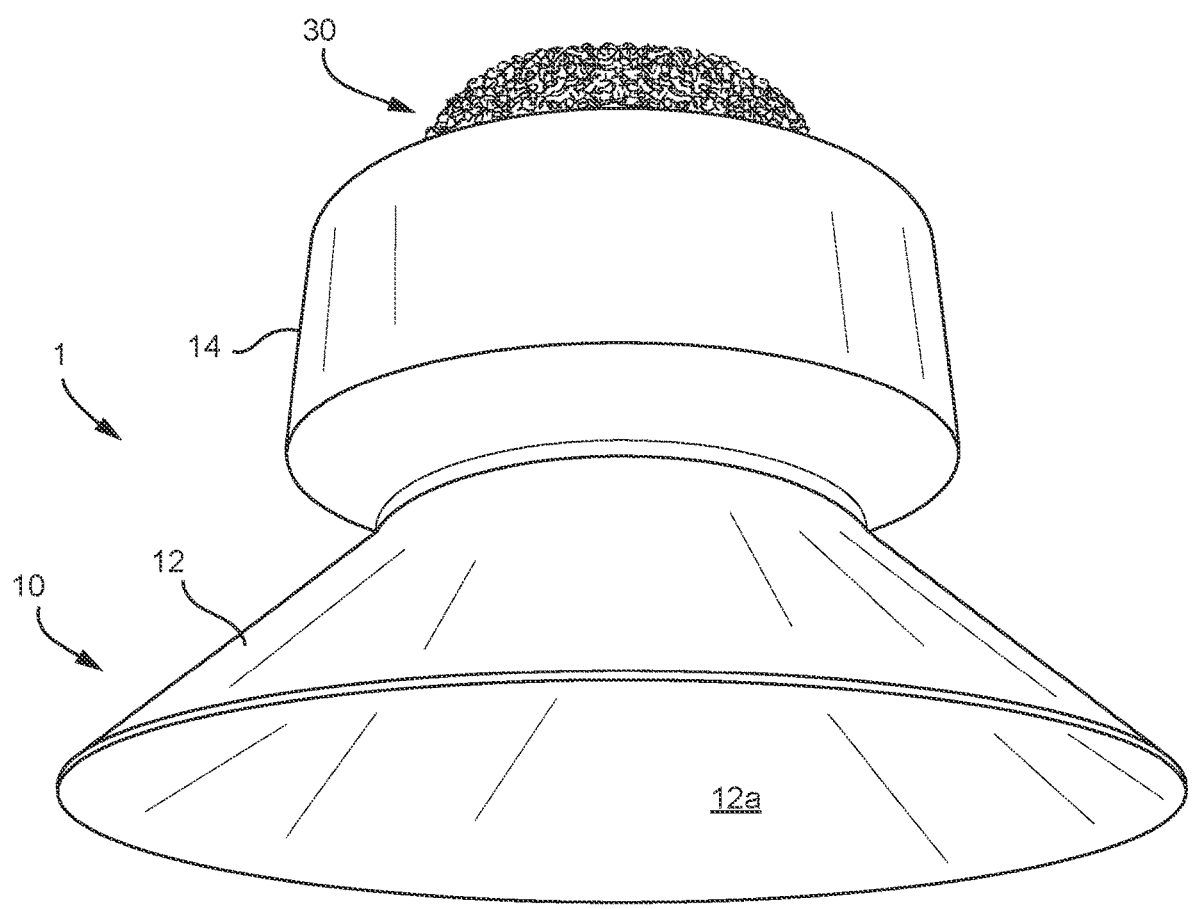
FIG. 1 shows an axonometric view of a lighting device according to an embodiment of the present invention.
Figure 2:
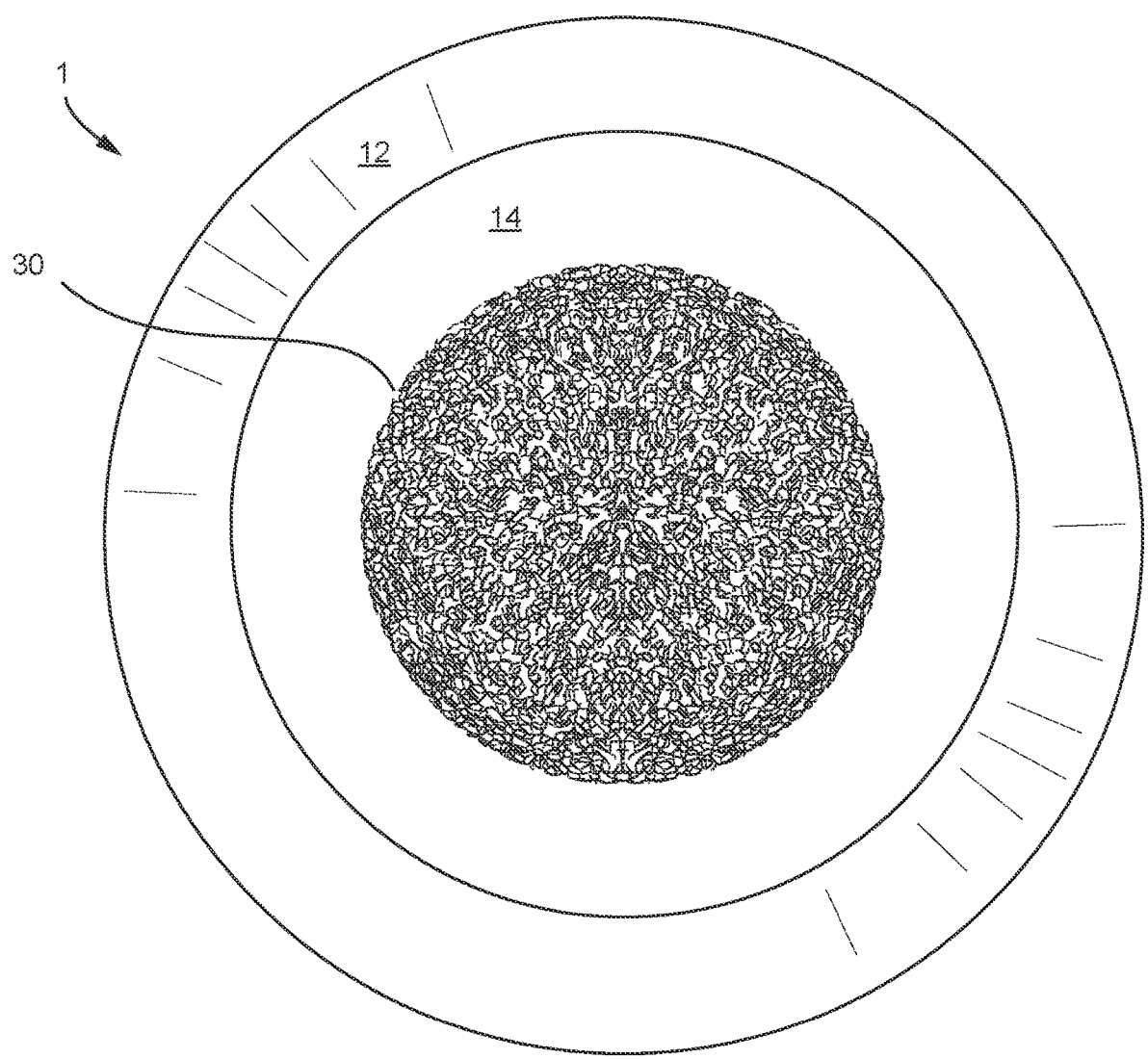
FIG. 2 shows a top plan view of the lighting device according to FIG. 1.
Figure 3:
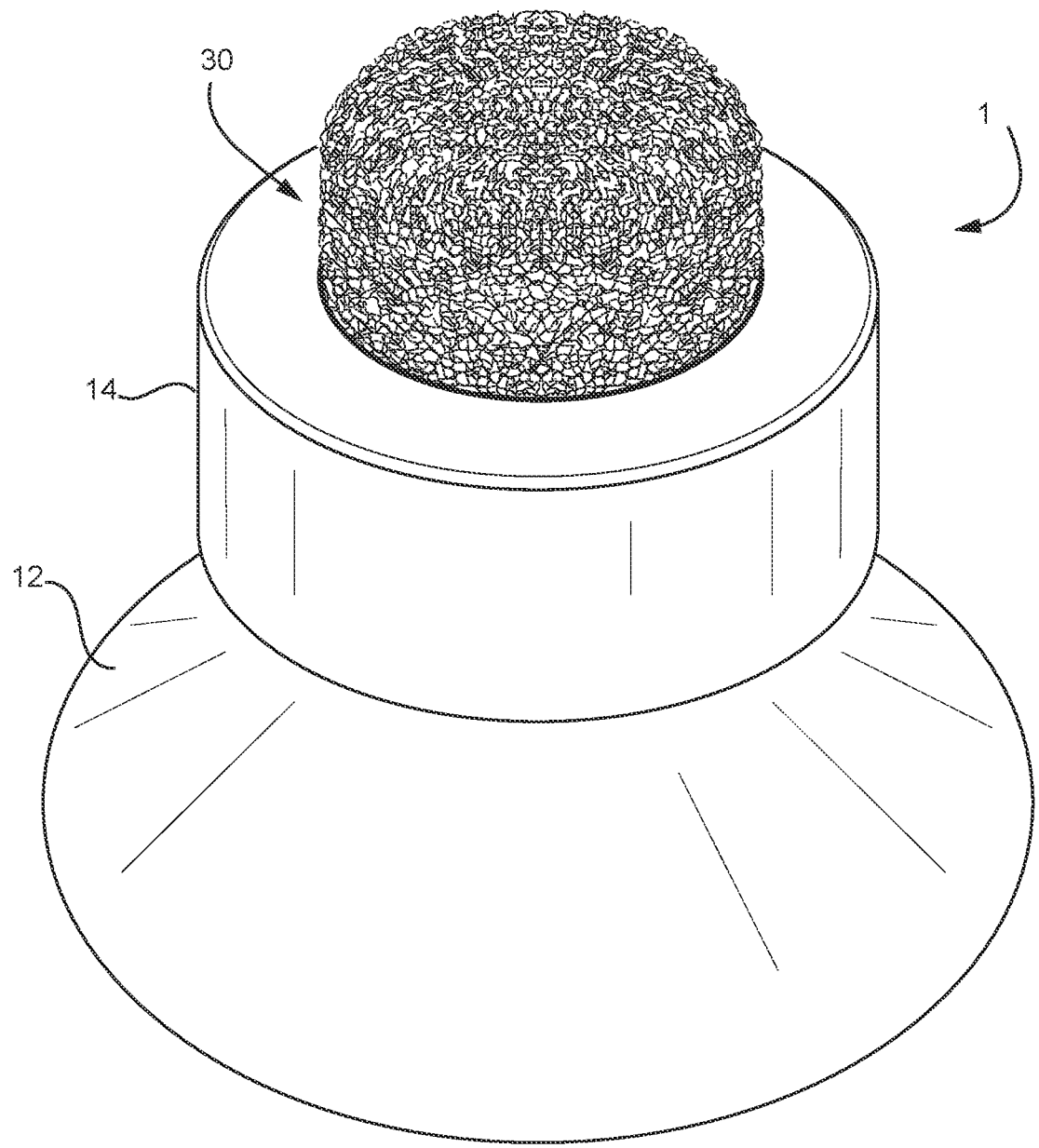
FIG. 3 shows another axonometric view of the lighting device according to FIG. 1.
Figure 5A:
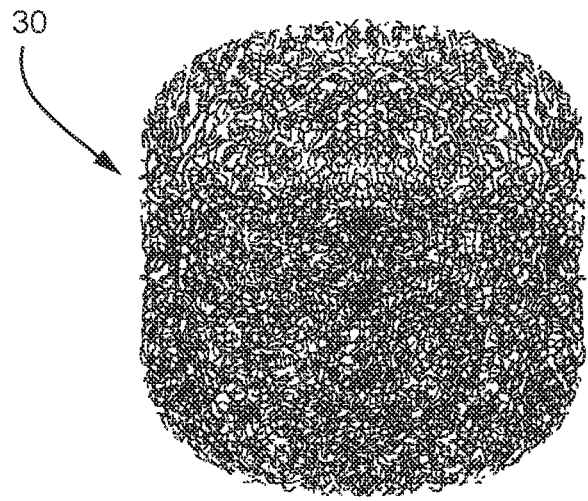
FIGS. 5a-5c show three different views of an embodiment of the filter.
Figure 5B:
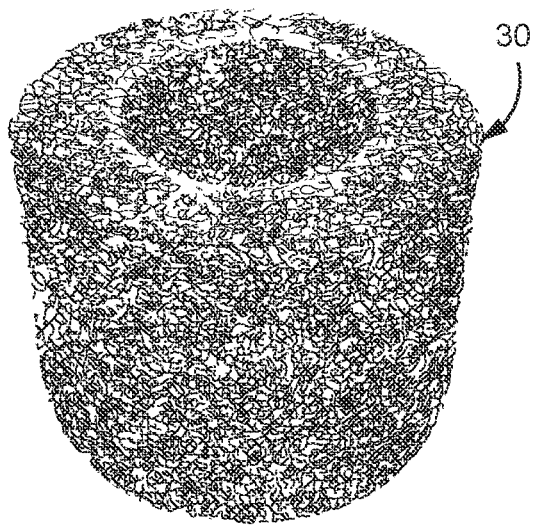
Figure 5C:
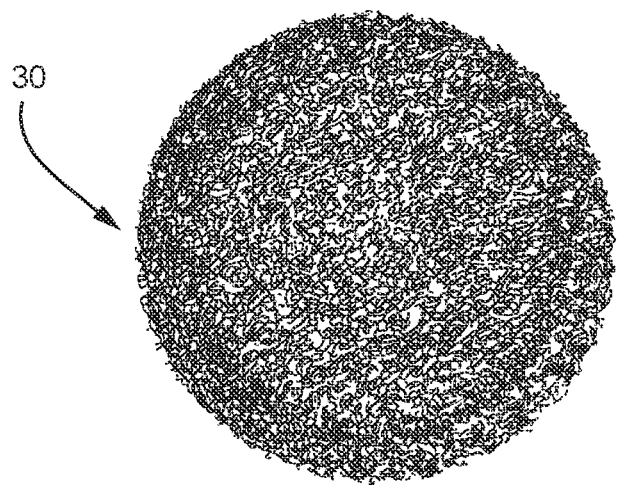

In the present description and in the attached claims, the term "lighting device" is understood as referring to a lamp, chandelier or the like, irrespective as the shape of the body (in particular the reflecting body), the attachment or support method and the type of technology of the lighting body. For example, it may be a chandelier hung from the ceiling, a floor lamp, a wall lamp or a desk lamp. The lighting body may be of the LED type or other technology.

In the present description and in the attached claims, the term "antimicrobial anodization" is understood as referring to any electrochemical anodization treatment designed to form a porous layer of oxide on the surface of the treated metal, followed by treatment with antimicrobial substances deposited in the pores included in the aforementioned porous layer.

In the present description and in the attached claims, the term "threadlike element" will be used to indicate an element in which the length is greater than the cross-section. The expression "threadlike element" for example will be used to indicate a wire with a circular (or similar) cross-section or a flat strip. Said threadlike element is therefore characterized by a high "aspect ratio". The "aspect ratio" is the ratio between the longer dimension and the shorter dimension of a two-dimensional figure, but this concept may also be extended to three-dimensional geometrical figures, choosing two characteristic dimensions of the solid figure. The "aspect ratio" of a threadlike element may therefore be defined as being the ratio between its length and the diameter of the cross-section, assuming a circular cross-section, or the smallest dimension of the cross-section.

In the present description and in the attached claims, the term "non-permanent contact" is understood as referring to the relative arrangement of the threadlike elements. In particular, a non-permanent contact, for the purposes of the present description and the claims, is a bearing contact, possibly with interference. In this non-permanent contact, the threadlike elements are mainly in contact with each other without welds, adhesives, rivets, screws, fasteners or the like. A non-permanent contact may also be typically formed by means of deformation of the threadlike elements.

In the present description and in the attached claims, the term "randomly deformed", referring to the threadlike elements, is understood as referring to threadlike elements when observed in the filter. A deformation is random when it does not have any evident periodicity. For example, when a bundled mass of threadlike elements may be observed. This bundled mass of threadlike elements creates a plurality of pathways which are partly (and mainly) non-linear. In other words, observing the filter, a prevalence of linear pathways created by the relative position of the threadlike elements may not be recognized.

FIGS. 1-4 show a view of a lighting device 1 according to an embodiment of the present invention. Obviously, the form of the lighting device 1 is an example and the present invention is not limited to this form. The present invention is not even limited by the type of lighting device and/or by its ceiling fastening system.

The lighting device 1 comprises a main body 10, a lighting body 20 and a filter 30.

The main body 10 of the embodiment shown comprises a frustoconical bottom part 12 and a substantially cylindrical top part 14. Preferably, the inner surface 12a of the bottom part 12 is at least partly light-reflective.

The lighting body 20 is configured so as to emit light 7, for example downwards, so that it is at least partially reflected by the inner surface 12a of the bottom part 12.

The filter 30 is arranged so as to receive an air flow A to be filtered. The air flow A may be generated by an active mechanical system such as a fan operated by an electric motor. The fan may be external to the lighting device 1 (for example the fan of an air treatment unit (ATU) or a fan coil. Alternatively, the fan may be incorporated in the lighting device or in any case connected to it.

Alternatively the air flow A is generated by a movement of layers of air at different temperatures. Preferably, the air flow A is generated by a movement of layers of air which is at least partially generated by the heating of air C caused by the lighting body 20. However, the air flow A may be generated by a room heating system (floor, radiator or hot air type).

By way of a further alternative, the air flow A may be generated by a combination of an active mechanical system (fan or the like) and passive system (heating of the lighting body).

According to the present invention, the lighting device 1 is configured so as to form a conveying channel 13 for directing air A to be filtered towards the filter 30 and so as to cause the air A to pass (naturally or by means of force) through said filter 30. The schematic cross-section shown in FIG. 4 shows, by means of a curved line with arrows, the path of the air A. The ambient air is drawn upwards, causing it to pass first (naturally or with force) through the conveying channel 13 and then into the filter 30. In this way the air A is treated by the filter 30 and purified.

In the embodiment shown in FIGS. 1-5, the filter 30 has a roughly doughnut-like form, but with a closed bottom and with the opening directed downwards. Advantageously, it may be inset in a seat 15 formed in the top of the upper part 14 of the main body. The seat 15 preferably comprises an opening 16.

Figure 6:
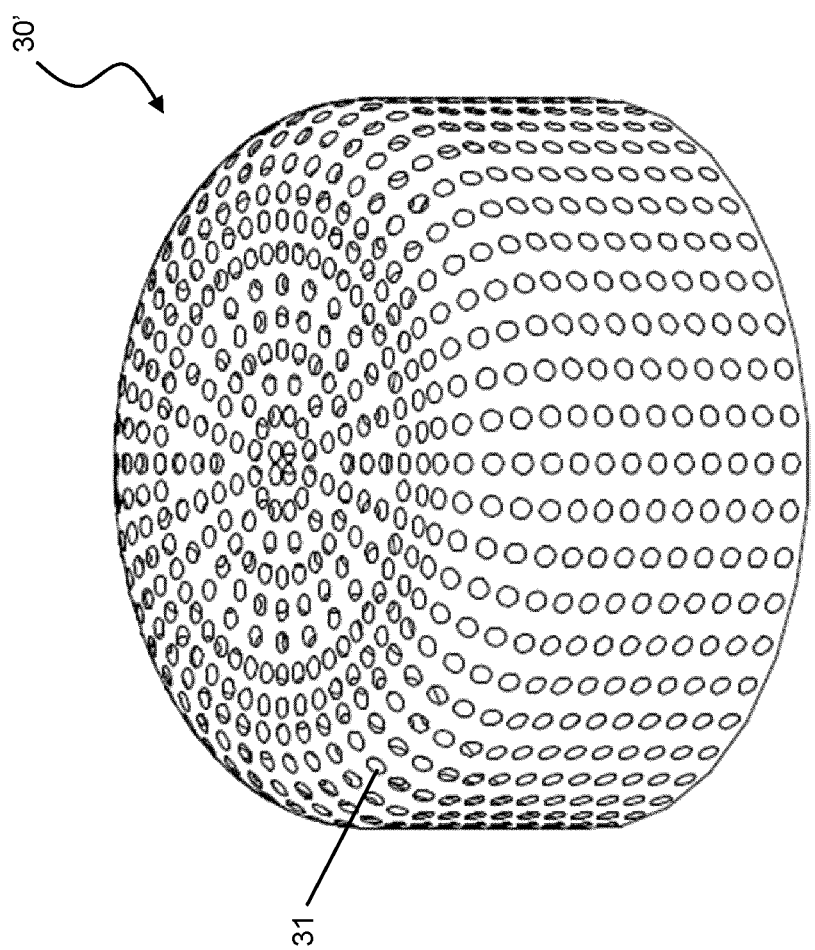
FIG. 6 shows a second embodiment of filter.

According to an embodiment, shown in FIG. 6, the filter 30', is formed by a suitably pressed metal sheet provided with a plurality of holes 31. In this second embodiment also, advantageously the filter 30' may be inset in the seat 15 formed in the top of the upper part 14 of the main body.

Figure 8:
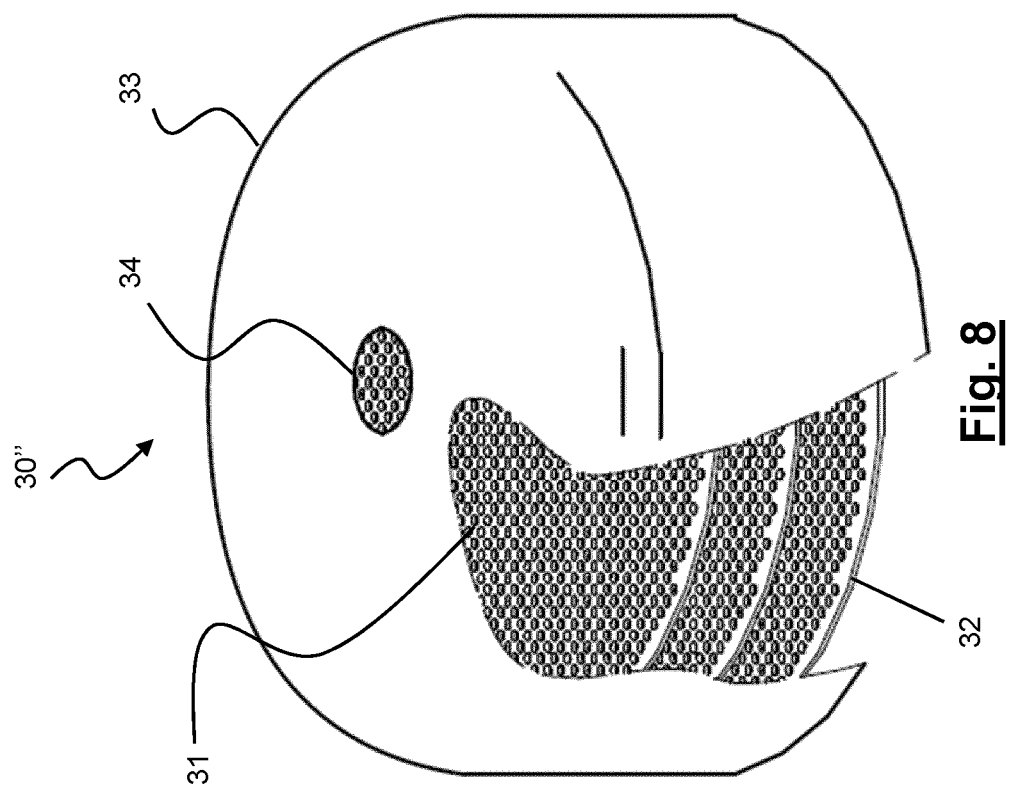
FIG. 8 shows, partially cross-sectioned, a third embodiment of filter.
Figure 7:
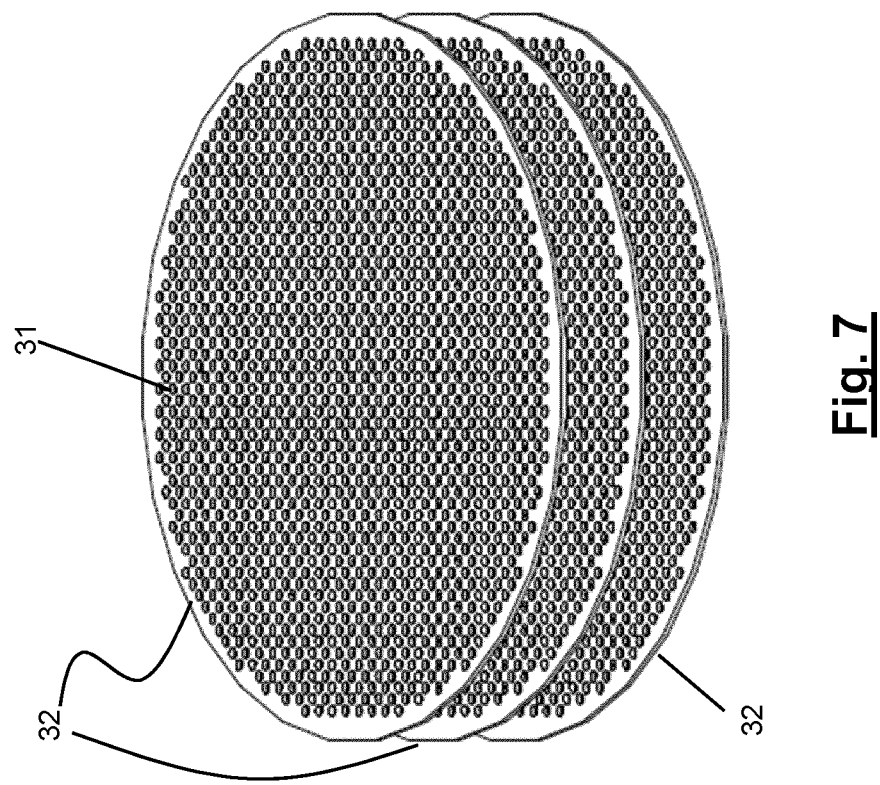
FIG. 7 shows three metal sheets with holes forming a filter according to a third embodiment.

According to a further embodiment (FIGS. 7 and 8), the filter 30" is formed by a stack of metal sheets 32 with suitably spaced holes 31 which advantageously may be inset in the seat 15 formed in the top of the upper part 14 of the main body.

Said stacked metal sheets 32 may be advantageously contained inside an additional body 33 with a central hole 34. The body 33 is preferably made of metal, treated in a manner similar to that of the filter 30. The form of the additional body 33 is designed to contain the flow of the fluid, forcing it to pass between the various sheet-metal layers 32 which create the appropriate winding effect. The air flow is at the end conveyed towards an upper hole.

The filter 30 is a filter made of anodized metal. The metal comprises a superficial porous layer of an oxide of said metal comprising at least one antimicrobial substance. The filter comprises a plurality of threadlike elements of said anodized metal, at least partially in non-permanent contact with each other, randomly deformed to form a plurality of non-linear pathways.

Preferably, said threadlike elements are deformed by means of a mechanical action, which may also be manual, until a disorderly bundled mass with a plurality of non-linear pathways is obtained.

The formation in the filter of said plurality of non-linear pathways has the effect of preventing the treated air from passing freely through the filter. In other words, the air which passes through the filter will be channeled along winding paths resulting from the arrangement of said threadlike elements. These winding paths increase the contact between the treated air and the anodized metal comprising at least one antimicrobial substance, therefore maximizing the antimicrobial action of the present filter.

The filter 30 may be made with a vast range of forms, depending on the prechosen application. In particular, a greater compactness of the filter made and greater total surface area of the metal threadlike elements will result in a more effective filtering and antimicrobial action.

Preferably, said threadlike elements are present in the form of woven elements, for example sections of metallic mesh, obtained from the weaving of the metal threadlike elements by means of a special apparatus.

Methods for the production of woven metal elements are known in the art and the person skilled in the art will be able to use the most appropriate method for the desired application. In particular, said woven elements may be made with a flat or tubular form.

Preferably, said woven elements are obtained from a tubular metallic mesh obtained by means of weaving of metal wire using a needle rotor machine.

According to embodiments, the metallic mesh is cut into sections of variable length, which are then assembled depending on the form with which the filter is to be made.

According to other embodiments, the filter 30' may be made of suitably cut and pressed aluminum sheet metal provided with a plurality of holes 31 so as to create a winding effect which may influence the passage of the flow.

The metal sheet could have a thickness of between 0.8 and 2 mm and the holes could have a diameter of between 0.5 and 10 mm.

Advantageously the filter could be composed of a plurality of perforated disks 32 arranged on top of each other and suitably spaced and positioned so as to increase the winding density of the filter. In this connection the disks 32 may be positioned so that the holes are never vertically aligned (nor coaxial with each other) and do not have the same diameter, so as to obtain a more chaotic flow.

The description which follows relates in particular to the first embodiment of the filter, but applies similarly to the other embodiments. Preferably, the metal used for the filter is aluminum or an alloy thereof.

The anodized aluminum or aluminum alloy mesh or sheet metal filter comprises a superficial, porous, aluminum oxide layer comprising at least one antimicrobial substance. The filter comprises a plurality of sections of said mesh at least partially in non-permanent contact with each other and randomly deformed to form a plurality of non-linear pathways.

The superficial porous layer extends at least partially inside the aluminum part and has a total thickness of about 2-40 µm, preferably 5-35 µm, even more preferably 10-20 µm. The pores present in the porous layer have preferably a diameter of between 5 nm and 100 nm.

The superficial porous layer comprises at least one bactericidal substance, chosen from among silver ions, copper ions, antibiotics, antifungal agents and antiviral agents. In a particularly preferred embodiment, the superficial porous layer comprises silver ions.

The antimicrobial substance is present inside said superficial porous layer in an amount sufficient to provide the finished product with an effective antimicrobial action. Preferably, said antimicrobial substance occupies between 10% and 90% of the total volume of the pores present in said superficial layer, calculated per unit of surface.

Optionally, said superficial porous layer may also comprise a coloring agent.

Said superficial porous layer comprising at least one antimicrobial substance is formed on the metal used in the present invention by means of an anodization process and an antimicrobial treatment, namely an antimicrobial anodization treatment.

This antimicrobial anodization process may be advantageously carried out on the threadlike elements before or after deformation, as well as on the woven elements, or finally on the finished filter.

Said process may be advantageously carried out also on perforated sheet-metal or mesh elements.

According to a particularly preferred aspect, the antimicrobial anodization process is carried out on the finished filter, before or after pressing. In this way it is possible to exploit, during the entire filter production process, the properties of the metal such as, in particular, the optimum machinability in the case of aluminum or aluminum alloy, which is typically decreased by the anodization process, and at the same time simplify the antimicrobial anodization operations, carrying them out on small-size parts instead of on long lengths of wire or mesh, with a consequent reduction in terms of the time and costs of the reagents required.

Advantageously, the anodization process and the antimicrobial treatment may be performed in a single step or in two successive steps. Preferably, the anodization process and the antimicrobial treatment are performed in a single step.

The process for anodization of metals, and in particular aluminum or aluminum alloys, is well-known to the person skilled in the art and any procedure able to form a superficial porous layer on the metal is useful for the purposes of the present invention. The person skilled in the art will be able to choose the most suitable anodization process.

Preferably, the aluminum or aluminum alloy anodization process is performed by immersing the article to be anodized inside a bath containing an aqueous solution of sulfuric, oxalic or chromic acid, in a concentration of between 2% and 20% v/v. A current of 0.1-2 A/dm$^2$ is applied to the aluminum for a time sufficient to obtain a layer of the desired thickness over the entire surface of the article, typically 10-60 minutes, at a temperature of between 15° C. and 50° C.

Post-anodization antimicrobial treatments are known in the art and any procedure able to deposit an antimicrobial substance inside the pores formed on the superficial oxide layer is useful for the purposes of the present invention.

In a preferred embodiment, the antimicrobial substance consists of silver ions which are deposited by means of electrodeposition on the superficial porous layer which has formed during the anodization process. Preferably, said superficial porous layer comprising at least one antimicrobial substance is at least partially sealed, i.e. most of its surface is sealed.

Advantageously, the sealing operation may be performed at the same time as the antimicrobial treatment or during a following step.

The sealing process is also well-known to the persons skilled in the art. For example, in the case of aluminum or aluminum alloys, sealing may be performed by means of hydration of the aluminum oxide which forms the superficial porous layer. Said hydration is performed by immersing the aluminum in a bath of deionized water at a temperature of 100° C. for several hours, or by subjecting it to treatment with high humidity steam for several hours.

Optionally, the metal may be pre-treated, before the anodization step, using chemical and/or mechanical treatments designed to clean and finish the metal part. Treatments known in the art are for example brushing, designed to eliminate physical imperfections from the surface, degreasing—an operation necessary for obtaining a uniformly reactive surface—and descaling—a chemical treatment useful for eliminating grease, dirt and oxides which are already present and may interfere with the formation of the anodic film.

Optionally a coloring or electrocoloring treatment may be performed. This treatment may be performed during any one of the steps of the antimicrobial anodization process.

The invention claimed is:

1. A lighting device comprising a main body, a lighting member and a filter which is at least partially made of anodized metal for treating air, wherein said metal comprises a superficial porous layer of an oxide of said metal comprising at least one antimicrobial substance, wherein said filter comprises a plurality of threadlike elements of said anodized metal, at least partially in non-permanent contact with each other, randomly deformed to form a plurality of non-linear pathways, and/or a plurality of sheet metal disks with holes.

2. The lighting device according to claim 1, wherein said metal is aluminum or aluminum alloy.

3. The lighting device according to claim 1, wherein said antimicrobial substance consists of silver ions.

4. The lighting device according to claim 1, wherein said threadlike elements are present in the form of woven elements.

5. The lighting device according to claim 1, wherein said woven elements are sections of a metallic mesh.

6. The lighting device according to claim 4, wherein said woven elements have a flat or tubular form.

7. The lighting device according to claim 1, wherein said threadlike elements are deformed by means of pressing.

8. The lighting device according to claim 1, wherein said superficial porous layer is obtained on the finished filter, before or after pressing.

9. The lighting device according to claim 1, wherein said superficial porous layer is at least partially sealed.

10. The lighting device according to claim 1, further comprising a channel for channeling air to be treated towards said filter.

11. The lighting device according to claim 1, wherein the air to be treated passes through said filter owing to the effect of a difference in temperature and/or the action of a mechanical device.

12. The lighting device according to claim 1, wherein at least one hole of a first disk is not axially aligned with a corresponding hole of a second adjacent disk and/or a hole of a first disk has a different diameter from the diameter of a corresponding hole of a second adjacent disk.

\* \* \* \* \*